(12) United States Patent
Pavlovic et al.

(10) Patent No.: US 11,608,389 B2
(45) Date of Patent: Mar. 21, 2023

(54) F-FUCOIDAN, DESULFATED F-FUCOIDAN, AND ITS PROCESSED DERIVATIVES IN TERMS OF DESULFATED OLIGO-FUCOSE AS INHIBITORS OF GASTROINTESTINAL INFECTION

(71) Applicants: Bojan Pavlovic, Beograd (RS);
Franz-Georg Hanisch, Cologne (DE);
Cem Aydogan, Schindellegi-Feusisberg (CH)

(72) Inventors: Bojan Pavlovic, Beograd (RS);
Franz-Georg Hanisch, Cologne (DE);
Cem Aydogan, Schindellegi-Feusisberg (CH)

( * ) Notice: Subject to any disclaimer, the term of this patent is extended or adjusted under 35 U.S.C. 154(b) by 49 days.

(21) Appl. No.: 16/755,601

(22) PCT Filed: Oct. 5, 2018

(86) PCT No.: PCT/RS2018/000016
§ 371 (c)(1),
(2) Date: Apr. 13, 2020

(87) PCT Pub. No.: WO2019/074387
PCT Pub. Date: Apr. 18, 2019

(65) Prior Publication Data
US 2021/0017301 A1    Jan. 21, 2021

(30) Foreign Application Priority Data
Oct. 12, 2017   (RS) .................. P-2017/1030

(51) Int. Cl.
*C08B 37/00* (2006.01)
*A61K 31/737* (2006.01)

(52) U.S. Cl.
CPC ........ *C08B 37/0063* (2013.01); *A61K 31/737* (2013.01)

(58) Field of Classification Search
None
See application file for complete search history.

(56) References Cited

PUBLICATIONS

Yu, Food Chemistry 139 (2013) 702-709. (Year: 2013).*
Zhang, Thrombosis and Haemostasis 111.3/2014, pp. 429-437. (Year: 2014).*

* cited by examiner

*Primary Examiner* — Layla D Berry
(74) *Attorney, Agent, or Firm* — Mark M. Friedman

(57) ABSTRACT

The subject of this invention are native forms of fucoidan polysaccharide, desulfated fucoidan and derivatives obtained by processing to the level of fucose-oligosaccharides containing preferentially, but not exclusively less than 20 monosaccharide fucose units alpha-linked by a glycosidic bond, with an average molecular weight of preferentially less than 3 kDa. The poly- and oligosaccharides that are described according to the invention are natural and safe, and are used as a dietary supplement for the use in prevention and treatment of pathologies associated with Noroviruses or Rotaviruses, *Salmonella* sp. or *Pseudomonas aeruginosa* or *Campylobacter jejuni* and other enteroviruses and enteric pathogens that cause bacterial gastroenteritis, as well as in the food production process. The invention also relates to a method for the desulfation and fragmentation of fucoidans to generate desulfated poly- or oligo-fucoses.

5 Claims, 15 Drawing Sheets

Example 10
Fractionation of fucoidan
processing products
on BioGel-P2

Example 11B: MALDI mass spectrometry of fucoidan processing products
MS/MS spectrum of permethylated nonasaccharides from processed fucoidan Example 12: Linkage Analysis by GCMS of partially methylated alditol acetates (PMAA) from fucoidan processing products

F-FUCOIDAN, DESULFATED F-FUCOIDAN, AND ITS PROCESSED DERIVATIVES IN TERMS OF DESULFATED OLIGO-FUCOSE AS INHIBITORS OF GASTROINTESTINAL INFECTION

TECHNICAL FIELD

The present invention relates to native, desulfated and processed fucoidans, desulfated oligosaccharides or oligo-fucoses, isolated from natural materials (F-fucoidan), for the use in treatment or prophylaxis of gastroenteritis, infections caused by Noroviruses or Rotaviruses, *Salmonella* sp. or *Pseudomonas aeruginosa* or *Campylobacter jejuni* binding to blood-group glycans on mucins and mucin-type O-glycoproteins on epithelia of the gastrointestinal tract of mammals, and the process of their preparation. According to the IPC the invention belongs to the classes A61K 31/70, A61K 36/00, A61P 31/12, A61P 31/14, A61P 31/04.

Technical Problem

The invention described herein solves the problem of obtaining a cheap, safe and natural composition, which has a strong activity on neutralization of pathogens. By selecting the relevant process parameters in all stages of the technological process, it is possible to entirely carry out the desulfation of naturally sulfated polysaccharides, fucoidans, in order to obtain completely or partially desulfated fucoidan and fragments of the polysaccharide. In this way desulfated/processed fucoidan unexpectedly exhibits an enhanced antiviral and antibacterial therapeutic activity. The essential modification of natural F-fucoidan refers to the desulfation of the polysaccharide, as this demasks fucose ligands that contribute to high valency of the agent. Also, it has been observed that the activity of the desulfated oligosaccharide increases with a decrease in its number of monosaccharide units.

The invention provides an effective, safe, non-toxic and economical natural product which can be used as such as a dietary supplement for preventive purposes or for suppression of problems caused by Noroviruses, Rotaviruses, *Salmonella* sp., *Pseudomonas aeruginosa* and *Campylobacter jejuni*, both by adults and by children. These polysaccharides and derived oligosaccharides can also be used in industrial conditions in the manufacture of oysters and other foods that are at risk of infection by mentioned pathogens.

Noroviruses are the most common cause of acute gastroenteritis in humans, mutate rapidly, are highly contagious, easily get out of control and to a susceptible population can be fatal. Noroviruses, together with Rotaviruses, are the most frequent cause of virally induced acute gastoenteritis in human populations of developing and developed countries. The annual number of diarrhea-associated events in outpatients is estimated at 8 million in industrialized countries, with 0.5 million hospitalizations, and 9.0 millions hospitalizations in developing countries, with nearly 2 million deaths.

Norovirus infections and their symptoms represent one of the most common causes of death worldwide for children under the age of three. In the year 2011 alone, more than 15.000 infections have been reported with infants (age 0 to 12 months) in Germany; with about 20 million infections worldwide. More than 200.000 cases of infant deaths are estimated to be caused by a Norovirus-infections.

It is generally impossible to predict the number of persons who get sick in one season, because it has been observed that in some years that number may exceed 100% of the number of cases from the previous year. It should be added that it is estimated that for every reported case there can be about 300 undocumented ones, because the vast majority of patients who have milder symptoms does not seek medical attention. Thus, for example, in 2013 in the UK it was estimated that the number of patients exceeded as much as 1.2 million in the first month of the epidemic.

Although other studies have shown that up to 90% of the adults tested so far do have antibodies against Noroviruses, it has also been found that the immunity is incomplete and lasts for approximately only 6 months, and, thus does not provide protection even against a reinfection with the same infectious strain.

Noroviruses, genus in the family Caliciviridae, are simple non-enveloped viruses that contain a single-stranded RNA genome surrounded by a capsid. The capsid is formed by one major structural protein.

There is accumulating evidence that fucose, as a structural part of histo-blood group antigens or Lewis-like antigens, is recognized by the P domains of the virus capsid protein.

Although Norovirus-studies remain difficult to conduct due to the fact that no animal models exist, there has recently been developed a cell culture model for assessing their pathogenicity. Also, using recombinant virus particles and testing volunteers, the histo-blood group antigens (abbreviated with HBGA) serving as receptors for Noroviruses have been identified as initial targets for viral entry and initiation of the infection process. HBGA are complex oligosaccharides which are expressed on the surfaces of red blood cells, the gastric mucosa, the respiratory passages, urogenital system and the intestinal tract. The HBG antigen H1, which is encoded via FUT2, an alpha-1,2-fucosyltransferase, has been identified as the most important genetic predisposition: individuals with homozygous zero mutant alleles for FUT2 have been shown to be nearly resistant towards gastrointestinal infections caused by Noroviruses.

Similarly, infections caused by Rotaviruses are the second most common cause of severe diarrhoea among infants and young children. Rotavirus is a genus of double-stranded RNA virus belonging to the Reoviridae family. By the age of five, nearly every child in the world has been infected with Rotavirus at least once. As the Norovirus, the Rotavirus is transmitted mostly by the faecal-oral route.

More than 450.000 children worldwide under the age of five still die from Rotavirus infection each year, most of them living in developing countries, and almost two million more become severely ill. Although the incidence and severity of Rotavirus infections has declined in countries that have added a Rotavirus vaccine to their routine childhood immunisation policies, a vaccine that prevents infection of both, Norovirus and Rotavirus, would be highly valuable.

Up to today, there is neither a vaccine nor an available causal therapy to cure the Norovirus caused gastroenteritis. As a consequence, the treatment of Norovirus gastroenteritis is restricted to a supportive oral and parenteral rehydration with electrolytes.

The need for new substances and compositions with which the gastrointestinal infection caused by Noroviruses and pathogens with similar mechanisms of entry and tissue invasion, can be effectively prevented and treated, led to the object of the present invention.

BACKGROUND ART

The first isolation of "Fucoidan" from marine brown algae was reported 90 years ago (Killing, 1913). Thirty-five years later, evidence was published showing that fucans also occur in marine invertebrates (Vasseur, 1948). These polysaccharides, mainly constituted of sulfated L-fucose, are easily extracted from the cell walls of brown algae (i.e. Phaeophyceae) with hot water (Percival and Ross, 1950) or acid solutions (Black, 1954) and can account for more than 40% of the dry weight of isolated cell walls (Kloareg, 1984). In marine invertebrates, sulfated fucans occur in the egg jelly coat of sea urchins (Mulloy et al., 1994) and in the body wall of sea cucumbers (Mourão and Bastos, 1987). The fucans of brown algae, often called fucoidans, have been known for some time to act as modulators of coagulation, as have other algal polysaccharides (Chargaff et al., 1936). Fucoidan preparations have been proposed as alternatives to the anticoagulant heparin, which is prepared from mammalian mucosa; being of vegetable origin, they are less likely to contain infectious agents, such as viruses or prions. Like heparin, it has been shown that fucoidans also affect many biological activities such as: inflammation, cell proliferation and adhesion, viral infection, and fertilization (Boisson-Vidal et al., 1995).

However, relatively few studies have interpreted the biological activity of fucoidans in terms of molecular structure. Almost all biological studies use a commercially available, crude preparation of sulfated polysaccharides from *Fucus vesiculosus* rather than a purified fucoidan (Mulloy et al., 1994). Recent insights into the structures of fucans from different plant and animal species may help explain their mode of activity, whether as research reagents or as potential therapeutics.

Algal fucoidans are present in several orders, mainly Fucales and Laminariales but also in Chordariales, Dictyotales, Dictyosiphonales, Ectocarpales, and Scytosiphonales. In fact, they are widely present among all the brown algae (Phaeophyceae) so far investigated. On the other hand, fucoidans seem to be absent from green algae (Chlorophyceae), red algae (Rhodophyceae), and golden algae (Xanthophyceae), as well as from freshwater algae and terrestrial plants.

Anticoagulant and antithrombotic activities of fucoidan fractions (*A. nodosum*) increase with increasing molecular weight and sulfate content. However, fractions in which the native pattern of sulfation was intact were more potent than fractions of equivalent molecular weight and overall degree of sulfation in which this pattern had been disrupted by partial desulfation (Boisson-Vidal et al., 2000).

Fucoidan and low-molecular-weight fucoidans, but not desulfated fucoidans, inhibit *Plasmodium berghei* development in Hep G2 cells and sporozoite invasion of Chinese hamster ovary cells (Ying et al., 1997).

Specific enzymatic methods can be used to provide tailored oligosaccharides for biological studies, as well as for obtaining simplified samples from which it is possible to deduce the structure of the original fucoidan. Currently employed methods of chemical modifications prior to analysis (hydrolysis, desulfation, deacetylation) often require strong basic or acidic conditions at high temperature, which can modify the polysaccharide. For example, acetyl groups have been found in almost all the algal fucoidans studied in recent years (*C. filum, C. okamuranus, F. evanescens*) but may be removed during the preparation process (Chizov et al., 1999).

One study has shown a sulfatase able to act specifically on some sulfate groups of fucoidan (Daniel et al., 2001). This enzyme partially purified from the scallop *P. maximus* is able to release sulfate groups present at position 2 of monosulfated L-fucose, or of mono- and disulfated components of the disaccharide from *A. nodosum* fucoidan. In conjunction with the α-L-fucosidase purified from the same mollusc, it seems possible to increase the degradation of fucans (Berteau et al., 2002). These enzymes are therefore unique tools to produce selectively modified fucans, which could allow direct determination of the involvement of branches and sulfate groups in their biological activity.

Like many other sulfated polysaccharides, fucoidan can inhibit virus infection of cells. This has been demonstrated for Herpes simplex, cytomegalovirus, and human immunodeficiency virus (Hoshino et al., 1998) as well as bovine viral diarrhea virus (Iqbal et al., 2000), probably by competing with cell surface HS for binding to the virus. Some data were provided that point to therapeutic applicability in the context of cytomegalovirus infection, but this is strictly and totally dependent on the presence of sulfate on the polysaccharide, whereas our processing product should be completely or at least partially devoid of sulfate, as this protects (masks) the relevant fucose residues.

Marionneau et al. ("Norwalk Virus Binds to Histo-Blood Group Antigens Present on Gastroduodenal Epithelial Cells of Secretor Individuals", Gastroenterology (2002) 122: 1967-1977), have shown that recombinant Norovirus virus-like particles use carbohydrates present on human gastroduodenal epithelial cells as ligands.

Further, Morrow et al. ("Human Milk Oligosaccharides are associated with protection against Diarrhea in Breast-fed Infants", J. Pediatr. (2004) 145:297-303) have observed that *Campylobacter* and Calicivirus caused diarrhea occurred less often in infants who have been fed with milk containing high levels of 2-linked fucosyloligosaccharide as a percent of milk oligosaccharide.

In this connection, EP1689348(B1) (2003) discloses the use of oligosaccharide compositions, in particular of glycoproteins where 2-fucosyllactose is linked to human serum albumin, in the treatment of infections.

Therapeutic effect of milk oligosaccharides is well-known, so the application WO2010/120682 discloses milk oligosaccharides and use thereof in treating infections in animals. WO2012/092153 discloses nutritional composition comprising human milk oligosaccharides and nucleotides and uses thereof for treating and/or preventing enteric viral infection. WO2014/128057 discloses synthetic fucosylated oligosaccharide for use in the treatment or prophylaxis of an infection with Noroviruses or Rotaviruses of a mammal. The oligosaccharides that are described by this patent do not include only fucose but also galactose, glucose, related β1-4 and β1-3 glycosidic linkages as well as the N-acetylgalactosamine. The mixture of oligosaccharides derived from fucoidan and native fucoidan itself is more active than the milk oligosaccharides by about one order of magnitude, as will be shown in the description of the invention and the embodiments.

The most relevant literature close to the topic reports only on potential applications in the context of cytomegalovirus infections. (Wang et al. "The antiviral activities and mechanisms of marine polysaccharides: an overview." Mar Drugs. 2012; 12; 10(12):2795-816 and Li at al. "Fucoidan: structure and bioactivity" Molecules 2008; 12; 13(8):1671-95). These applications are dependent on native state sulfation of the polysaccharide. According to prior art knowledge desulfated polysaccharides or polysaccharide derived oligosaccharides are expectedly inactive in the respective (Noroviruses, Rotaviruses, *Salmonella* sp. *Pseudomonas aeruginosa* and *Campylobacter jejuni*) context. On the contrary, we show that sulfate residues are preferentially removed in the Norovirus context to demask the relevant fucose residues. More-over, the bioactivity of the polysaccharide is increased when the polysaccharide is fragmented to the level of oligosaccharides in the size range of up to about 20-mers (larger-sized oligosaccharides are still active, as holds true for native fucoidan).

The numerous papers deal with the partial acid hydrolysis of marine polysaccharides and also of the relevant polysaccharides from brown algae, but those procedures are not simple and effective enough to achieve both fragmentation and complete desulfation in one step. This is important because the products, desulfated oligosaccharides (oligofucoses), are characterized by their ability to block Norovirus' binding to human gastric mucin. (Pielesz at al. "Mild acid hydrolysis of fucoidan: characterization by electrophoresis and FT-Raman spectroscopy". Carbohydr. Res. 2011; 27; 346(13):1937-44 and Kusaykin at al. "Fucoidanases" Glycobiology. 2016; 26(1):3-12).

There are numerous papers which describe the particular binding mechanisms of Noroviruses of the relevant strains to terminal fucose that is part of blood group antigens, in particular to blood group H (Fucα1-2Gal) and eventually to blood group H2 antigen (Fucα1-2Gal1-4GlcNAc/Glc). (Koromyslova at al. "The sweet quartet: Binding of fucose to the norovirus capsid." Virology. 2015; 483:203-8, Singh at al. "Structural Evolution of the Emerging 2014-2015 GII.17 Noroviruses." 2015; 23; 90(5):2710-5, Chen at al. "Crystallography of a Lewis-binding norovirus, elucidation of strain-specificity to the polymorphic human histo-blood group antigens." Pathog. 2011; 7(7):e1002152 and Singh at al. "Human noroviruses" fondness for histo-blood group antigens." Virol. 2015; 89(4):2024-40).

Rotaviruses, besides Noroviruses, are the second most relevant virus type which is known to bind to blood group H antigens/oligosaccharides. Hence, it can be expected that rotavirus infection can be prevented by application of processed polysaccharide. The same holds true for *Pseudomonas* and *Salmonella* strains, as binding of both can be blocked by the blood group H-related milk oligosaccharide 2-fucosyllactose. (Tan at al. "Histo-bloodgroup antigens: a common niche for norovirus and rotavirus." Expert Rev Mol Med. 2014; 10; 16:e5, Weichert at al."Bioengineered 2'-fucosyllactose and 3-fucosyllactose inhibit the adhesion of *Pseudomonas aeruginosa* and other enteric pathogens, like *Campylobacter jejuni*, to human intestinal and respiratory cell lines." Nutr Res. 2013; 33(10):831-8, Wu at al. "Interactions of the fucose-specific *Pseudomonas aeruginosa* lectin, PA-IIL, with mammalian glycoconjugates bearing polyvalent Lewis(a) and ABH bloodgroup glycotopes" Biochimie. 2006; 88(10):1479-92 and Topin at al. "Deciphering the glycan preference of bacterial lectins by glycan array and molecular docking with validation by microcalorimetry and crystallography." PLoS One. 2013; 19; 8(8): e71149).

The following papers describe norovirus binding to blood group related antigens in animal gastrointestinal tracts (clams, mussels and oyster, pigs): Tian at al. "Norovirus recognizes histo-blood group antigens on gastrointestinal cells of clams, mussels, and oysters: a possible mechanism of bioaccumulation." Food Prot. 2007; 70(9):2140-7, Schaeffer at al. "Norovirus contamination on French marketed oysters." Food Microbiol. 2013; 2; 166(2):244-8, Thebault at al. "Infectivity of GI and GII noroviruses established from oyster related outbreaks." Epidemics. 2013; 5(2):98-110, Maalouf at al. "Distribution in tissue and seasonal variation of norovirus genogroup I and II ligands in oysters." H, Zakhour M, Le Pendu J, Le Saux J C, Atmar R L, Le Guyader F S. Appl. Environ. Microbiol. 2010; 76(16):5621-30 and Tian at al. "Binding of recombinant norovirus like particle to histo-blood group antigen on cells in the lumen of pig duodenum." P, Jiang X, Zhong W, Jensen H M, Brandi M, Bates A H, Engelbrektson A L, Mandrell R. Res Vet Sci. 2007; 83(3):410-8.

In the prior art there are also patents and applications relating to the brown algae *Laminaria japonica* in particular. So CN105147743 (2015) discloses the use of *laminaria* extracts for treating EV71 infectious diseases. The patent refers to a glucan (poly-glucose) health beneficial effects in the context of enterovirus (EV71). CN103665120 (2013) refers to preparation of a lectin from *Laminaria japonica*, CN102367282(B) (2011), CN102274247(B) (2011) and KR100485686(B) (2003) describe the preparation of a polysaccharide isolated from *Laminaria japonica* having no relationship to fucoidan. KR20090127785 (2008) refers to isolation of fucoidan from *Laminaria japonica*. All of these patents, describing different variants of fucoidan extraction and purification, are not in conflict with the relevant information provided by the proposed application. U.S. Pat. No. 9,241,951(B2) (2009) This invention relates to the improvement of gastrointestinal health, immunity and performance by direct dietary intervention with a composition comprising a glucan and/or a fucan. For those purposes, brown seaweed have been used, particularly Laminariaceae, Fucaceae and Lessoniaceae.

U.S. Pat. No. 5,646,130 (1995) discloses low molecular weight (less than 5 kDa) sulfated polysaccharides containing about 20 monosaccharide units. The oligosaccharides that are described by this patent include mannuronopyranose (manose) and glucuronic acid. Those oligosaccharides are used for the prevention and therapy of thrombosis-induced ischemic vascular diseases of heart and the central nervous system, for treating acute thrombosis-induced brain infarction, in coronary ischemia-induced angina, and for treating hyperlipoproteinemia and lowering the relative amount of cholesterol.

US2002019991(A) (1998) describes compositions containing an alfa 1,2-fucose and use thereof in the treatment and prevention of gastrointestinal infections caused by *Escherichia coli* and *Vibrio cholerae*.

U.S. Pat. No. 6,126,961(A) (1998) describes composition and method for reducing the colonization of animal intestines by *Salmonella* sp. and other bacterial pathogens, which includes a polysaccharide containing cis-hydroxy sugar units or a derivative thereof, or the monosaccharide ribose or rhamnose, or a derivative thereof, and an animal feed. The polysaccharide cis-hydroxy sugar units may be one or more of mannose, a mannose derivative, galactose, a galactose derivative, galactomannans, galactosamine, fucose and arabinose. The polysaccharides may be incorporated into an animal feed in the form of a food gum or other biopolymer.

JP5364352(B) (2003) discloses method for producing the desulfated and oligomerized fucoidan and includes subjecting fucoidan to fucoidan-assimilative bacteria having the respective activities of desulfating and oligomerizing fucoidan, i.e. bacteria belonging to the genus *Flavobacterium* such as *Flavobacterium limicola* NITE AP-674 or *Luteolibacter algae* AP-675, AP-676, or extract thereof. U.S. Pat. No. 6,140,481(B) (1994) describes a process for producing a desulfated polysaccharide with a silylating agent, and desulfated heparin. JP3497209(B) (1993) discloses method for caning out desulfation of a sulfated sugar in the presence of a silylating agent. The silylating agent is preferably 2-trimethylsiloxypento-2-ene-4-one. Pomin et al. ("Mild acid hydrolysis of sulfated fucans: a selective 2-desulfation reaction and an alternative approach for preparing tailored sulfated oligosaccharides", Glycobiology (2005) 15(12):1376-1385), describe partial desulfation.

US2005255564(A) (2002) process patent is referring to the fragmentation of sulfated fucans, i.e. an enzymatic approach that leaves sulfation intact.

WO2014170505(A) and U.S. Pat. No. 7,846,452(B) (A) disclose preparations and the composition of extracts of plant species and seaweed, including the *Fucus vesiculosus*, that are useful in immunity regulation. CN102936293 (B) (2012) describes microwave-based protocols for extraction and purification of fucoidan from *Fucus vesiculosus* and U.S. Pat. No. 9,447,199(B) (2014) from brown algae.

JPH01313433 (A) (1988) and EP0606882(A) (1993) describe anti-HIV activity, which is however highly dependent on sulfation of fucoidan.

Different chemical structures have been proposed for this polysaccharide, since its discovery by Killing. Polysaccharide fucoidan exists either as a homopolymer of fucose (F-fucoidan) or as a heteropolysaccharide. Its composition differs depending on the sources and seasonality. The chemical composition of most polysaccharide fucoidans is complex. According to their structure, the F-fucoidan can be divided into two groups depending on their sources: one group includes *Laminaria* species that have their central chains composed by (1→3)-linked α-L-fucopyranose residues; the second group includes polysaccharide fucoidans isolated from *Ascophyllum* and *Fucus* species that have their central chains composed of repeating (1-3) and (1→4) linked α-L-fucopyranose residues.

Some minor amounts of α-L-fucopyranose are (1-2) linked to fucoses of the core chains. Besides fucose and sulfate groups (F-fucoidans), the presence of monosaccharide residues such as mannose, galactose, glucose, xylose and uronic acids was shown for U-fucoidans. Sulfate residues are found at high densities, as every second fucose can be substituted.

Although the experimental work uses *Fucus vesiculosus* as a fucan source, the invention relates to the defined, partially or completely desulfated oligosaccharides without intending to be limited to this particular natural source. Potential sources can be all species of brown algae and seaweed, but also other marine animal or plant sources.

U.S. Pat. No. 7,838,004 B2 (US20060211652 A1) describes a method of partial hydrolysis of fucoidan to give the sulphonated form used to prepare an infant formula (US 20060210697 A1). The sources of these fucoidans are Japanese mozuka, Japanese kombu and Tongan limu moui.

Although, with the above background, there are currently different approaches to treat or prevent infections with Noroviruses and other enteric pathogens, no actual composition has yet been provided that would prove to be effective in such treatment/prophylaxis.

SUMMARY OF THE INVENTION

The invention relates to native F-fucoidans, desulfated F-fucoidans and novel desulfated oligosaccharides obtained by desulfation and fragmentation of F-fucoidans, which have low molecular weight and are optimally sized in the range of 20 or less monomer units of fucose, linked with alpha glycosidic bonds. Brown algae *Fucus vesiculosus* have been used as a source of fucans, but the invention does not intend to be limited just on them. It is known that the content of oligosaccharides in brown seaweed and other seafood is between 12 and 20%, making them suitable for isolation of oligosaharides at economical conditions.

The fucoidan represents a major component in brown algae (as for example in *F. vesiculosus*, where it represents 12% of the biomass). The brown seaweed *Laminaria japonica Aresch* (Laminariales) is one of the most important economic seaweeds cultured in China, and it is also widely distributed in japanese and korean cuisines. The utilization of *L. japonica* has been documented in traditional chinese medicine for more than one thousand years. Fucoidan has the advantage of being accessible in unrestricted amounts, at low costs, as it is easily extractable and can quickly be available on the market. From the before mentioned, the polysaccharide has no adverse (toxic) effects on human or animal health.

Publications known so far are related to the hydrolysis of polysaccharides derived from marine algae and their partial fragmentation, but none of them describe a simple and efficient process in which the fragmentation could be carried out in one step with a complete desulfation of fucoidan. Desulfated F-Fucoidan, desulfated oligosaccharides derived thereof (oligo-fucoses) which besides the native polysaccharide are the preferential subject of the present invention, are specific in their ability to competitively block the binding of Noroviruses and other enteric pathogens with similar infection routes that use binding to blood-group H antigen. A method that produces well-defined desulfated poly- and oligosaccharides is economical, simple and efficient—both the complete desulfation alone or combined with fragmentation of the polysaccharide can be carried out in only one step.

The extraction of F-fucoidan from brown algae *Fucus vesiculosus* was carried out in the usual way that is used for the extraction of other sulfate oligosaccharides from macroalgae which starts with hot water, and the precipitation is done with salts or organic solvents.

This type of extraction can obtain yields of fucoidan (%) ranging from 0.26% to 20% of algal biomass dry weight. The physico-chemical characteristics of the extracted fucoidan polysaccharides are dependent on the severity of the treatments in the extraction such as: temperature, reaction time, concentration of chemicals, as well as on inherent factors of algae, such as species and size of algae, local climate and environmental factors.

According to the present invention, the process for the production of desulfated F-Fucoidan refers to a single chemical treatment of the neutral, dry pyrimidinium salt that is treated with a mixture of dimethyl sulfoxide/pyridine (5:12, v:v) at 110° C. for 9 h to liberate sulfate by solvolysis. The product is extensively dialysed to remove organic reagents and dried by vacuum rotation.

According to the present invention, the process for the production of desulfated low-mass oligosaccharides from fucoidan refers to a desulfation/fragmentation that is carried out by partial acid hydrolysis catalyzed either by mineral or organic acids or by a soluble, high molecular mass polystyrenesulfonic acid that allows separation of the low-mass oligo-fucoses from the acid by dialysis/ultrafiltration. By continuous removal of the products and entrapment on graphitized carbon their size can be controlled by the cut-off of the respective dialysis or ultrafiltration membranes. The entire process is continuous and is easily scalable to an industrial process.

According to the present invention, processing of F-fucoidan also covers workup steps dependent on the mode of partial acid hydrolysis: one of neutralization after drying by vacuum evaporation of volatile acids (during acid-catalyzed desulfation sulphuric acid is formed and needs to be neutralized). It can also comprise subfractionation by ultrafiltration to enrich the relevant oligosaccharide fraction or solid-phase extraction on graphitized carbon (Carbograph cartridges). Further alternatives could comprise the application of gel permeation chromatography (GPC) to subfractionate the glycans or to desalt the glycan fraction by group fractionation. Similarly, a further fractionation of the glycans could be achieved by polar-phase chromatography on amino-, amid- or diol-phases (HILIC).

Although the antiviral activities of fucoidans are well-known, it must be stressed that these activities are highly dependent on their sulfation (CMV, HIV) and their mechanistic mode of action is not related to carbohydrate blood-group competition. The native (sulfated) fucoidan compared to the desulfated or processed derivative is less active when it comes to pathogens that cause gastroenteritis.

Noroviruses of the relevant strains bind in particular to terminal fucose that is part of blood-group antigens, in particular H1 antigen (Fucα1-2Galβ1-3GlcNAc) and eventually, but less to H2 antigen (Fucα1-2Gal1-4GlcNAc).

Rotaviruses, besides noroviruses, are the second most relevant virus type which are known to bind to blood group H antigens/oligosaccharides. Hence, it can be expected that a Rotavirus infection can also be prevented by application of polysaccharides processed in the described way. The same holds true for *Pseudomonas aeruginosa, Campylobacter jejuni* and *Salmonella* sp. strains, as binding of these can be blocked by the blood group H-related milk oligosaccharide 2-fucosyllactose.

Microbially produced milk oligosaccharides, like 2-fucosyllactose, are currently approaching market approval as additives in infant formulas and have shown some protective value.

The novelty of our invention relates to documented evidence that the sulfate-group of the polyfucose does not play a role in the Norovirus blocking effect, on the contrary, it is more advantageous to remove it, as less substituted fucose becomes more accessible in this way. The structure of desulfated polysaccharide or oligosaccharide blocks viral binding by competition with blood-group related carbohydrates. According to the invention, the bioactivity of the desulfated polysaccharide increases.

Therapeutical activity of this desulfated oligosaccharide can be applied on all variants of Noroviruses that are of relevance in human infection (GII.4 from 1974 or 2012, GII.10 and GII.17), but also on those viruses that use similar or identical entry routes by binding to blood-group H related oligosaccharides on epithelia, like Rotaviruses. The target virus for the described antiviral agent is Norovirus, but also Rotavirus or other enteric pathogens that use similar routes of infection, like *Salmonella* sp., *Pseudomonas aeruginosa* and *Campylobacter jejuni*. All of these pathogens can also cause an infection by binding to blood-group glycans on mucins and mucin-type O-glycoproteins on epithelia of the gastrointestinal tract.

According to the invention, desulfated polysaccharide and oligosaccharides exert strong inhibitory potency against Noroviruses and their divergent strains binding to epithelia. In particular, the human pathogens GII.4 (Sydney 2012), GII.4 (CHDC 1974), GII.17 and GII.10 were investigated as virus-like particles (VLPs) with processed plant fucoidan in direct binding assays or in binding inhibition studies on human gastric mucins (Lewis blood-group defined) and/or in binding and inhibition studies using neoglycolipids derived from human milk oligosaccharides for capsid binding.

Different preparations of the Fucoidan from brown algae are shown to exert inhibitory potencies, whereas a significant increase is found after desulfation of the polysaccharide by solvolysis in DMSO/pyridine (5:12, v:v) for 9 h at 100° C. or by processing of the native material by partial acid hydrolysis in 0.01 M HCl (60° C., 4 h), which results in complete desulfation and partial fragmentation. Chloric acid can be replaced by other acids (for example formic acid or acetic acid) used at 0.1 M (60° C., overnight) or using variant parameters that result in similar fragmentation and desulfation. A further variant of simultaneous desulfation and fragmentation that is also based on partial acid hydrolysis uses a soluble, high-molecular mass polystyrenesulfonic acid (PSSA) that allows a size-based separation of the processing products (oligofucoses) by continuous dialysis and entrapment on graphitized carbon. Desulfation can be also achieved by treatment with sulfatases, whereas fucoidanases can be used for partial fragmentation of the polysaccharide.

The invention is based on the core evidence that structural elements of a natural polysaccharide (fucoidan) exert competitive inhibition effects on norovirus capsid binding to human gastric mucins. The evidence is based technically on ELISA format assays using VLPs of the most relevant norovirus strains, which all showed similar strong binding to gastric mucin and were blocked with similar effectivity by a blood-group-unrelated polysaccharide and processing products derived thereof.

Structural evidence of active glycans or partial structures of fucoidan was obtained from MALDI mass spectrometry (MS and MS/MS) of native and permethylated oligosaccharides, and moreover from linkage analyses by GC-MS. The active fraction with highest inhibitory effect is composed of oligosaccharides up to icosasaccharides (20-mers) containing the structural elements:

Fuc1-2Fuc, Fuc1-3Fuc, Fuc1-4Fuc, Fuc1-2Fuc1-3Fuc, Fuc1-2(Fuc1-3)Fuc, Fuc1-2(Fuc1-4)Fuc, Fuc1-3(Fuc1-2)Fuc, and Fuc1-2Fuc1-3(Fuc1-4)Fuc. The quantitatively dominating fucose oligomer varies in the size range from penta- to decamers. The anomeric configuration of fucose is alpha. Any of the above defined structural elements are not identical with or even related to the known blood-group H1 or H2 structures. On the contrary, even L-Fucα1-2-L-Fuc (fucose being identical to a 6-deoxygalactose) is strikingly different in structure compared to L-Fuc1-2-D-Gal, as the subterminal sugar is of L vs. D configuration.

According to the invention, desulfated or partially desulfated oligosaccharides in the optimal size range of up to 20-mers are shown to be highly potent inhibitors of Norovirus binding to gastrointestinal epithelia in humans.

BRIEF DESCRIPTION OF THE FIGURES

FIG. 1 is a line chart showing results from a duplicate assay at varying fucoidan concentrations;

FIG. 2 is a bar chart depicting B, C, Binding of GII.4 (Sydney 2012) VLPs to human gastric mucin (HGM) at pH 7.4 (B) and at pH 1.5 to 5.5 (C);

FIG. 3 is a bar chart depicting D, Variation of blocking conditions for binding assays of GII.4 to HGM (5% skim milk/PBS vs. 5% BSA/PBS;

FIG. 4 is a bar chart depicting Triplicate assay with fixed inhibitor concentration (10 mg/ml);

FIG. 5 is a bar chart depicting Triplicate assay with fixed inhibitor concentration (5 mg/mL);

FIG. 6 is line chart depicting neutralization and solubilization in capsid binding buffer (0.01% Tween-20/PBS) at varying concentrations;

BEST MODE OF CARRYING OUT THE INVENTION

Thus, with Fucoidan, desulfated Fucoidan and the Fucoidan-derived desulfated oligosaccharides that are the subject of this invention, infections by Noroviruses, Rotaviruses, *Salmonella* sp., *Pseudomonas aeruginosa* or *Campylobacter jejuni* can efficiently be prevented and/or treated.

This invention also relates to the use of native Fucoidan, desulfated Fucoidan or the derived desulfated oligosaccharides as prophylactic and therapeutic agents (food additives) that can be applied during epidemic phases in hospitals, or outside, in order to prevent infections caused by Noroviruses, as they block viral binding to gastrointestinal epithelia. Fucoidan, desulfated Fucoidan or the derived desulfated oligosaccharides can also be used as prophylactic and therapeutic agents (food additives) during other infections caused by other pathogens, such as Rotaviruses, *Salmonella* sp., *Pseudomonas aeruginosa* and *Campylobacter jejuni*, which generally have the same pathogen entry route mediated by blood group H-like carbohydrate structures. The Norovirus contamination of oysters can also be abolished by washing the oysters with solutions of native, desulfated or processed Fucoidans, which should make them highly valuable in industrial (oyster) application.

The following examples illustrate the inventive concept, in accordance with the description of the invention revealed in this patent, regarding the competitive affinity of desulfated oligosaccharides and providing the inhibition of pathogen binding whenever the infection is mediated by blood-group H-like carbohydrate structures, in order to reduce intestinal retention of the pathogens such as Noroviruses, Rotaviruses, Salmonela sp., *Pseudomonas aeruginosa* or *Campylobacter jejuni*. It is to be understood that these examples are provided by way of illustration only, and nothing therein should be taken as a limitation upon the overall scope of the invention.

The invention will be illustrated further on by the embodiments without intending to limit on them.

Example 1—Binding of GII.4 VLPs on Immobilized Native F-Fucoidan

A, Binding of GII.4 (Sydney 2012) VLPs on immobilized native F-fucoidan.

Figure 1:

Fucoidan was immobilized by drying from an ammonium hydrogencarbonate solution onto polystyrene microtitration plates. Blocking was performed with 5% BSA/PBS. VLPs were dispersed in 0.05% Tween-20/PBS (10 µg/ml according to protein content). Incubation conditions of binding assay were throughout 1 h at 37° C. for VLPs, primary antibody (anti-GII.4, rabbit polyclonal, 1:3000), and secondary antibody (anti-rabbit-Ig-alkaline phosphatase, 1:5000). Substrate p-nitrophenylphosphate (5 mg/ml) was incubated generally for 30 min at RT and color formation was measured at 405 nm. The figure (FIG. 1.) shows results from a duplicate assay at varying fucoidan concentrations.

Figure 2:
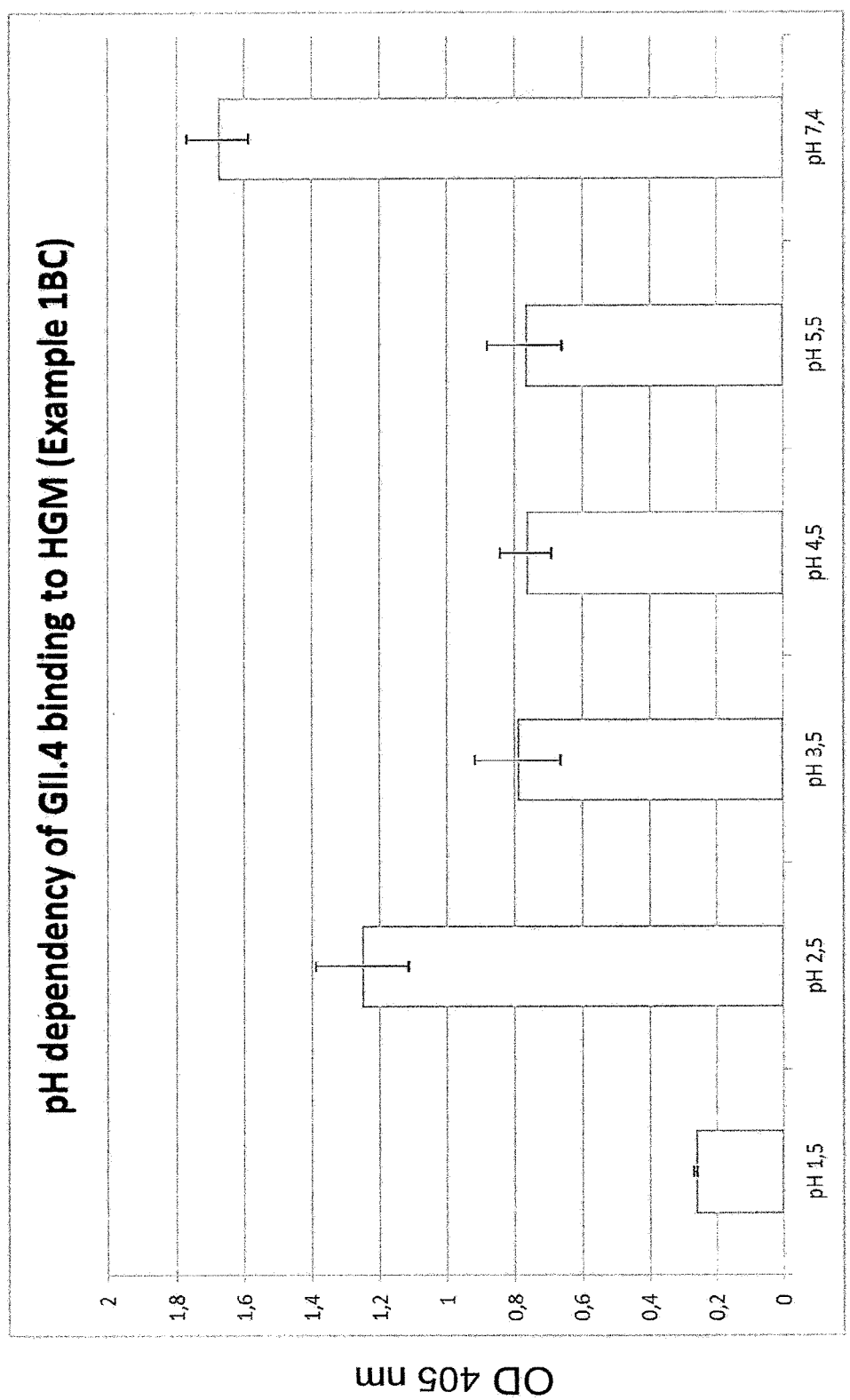

B, C, Binding of GII.4 (Sydney 2012) VLPs to human gastric mucin (HGM) at pH 7.4 (B) and at pH 1.5 to 5.5 (C); (FIG. 2.)

Figure 3:
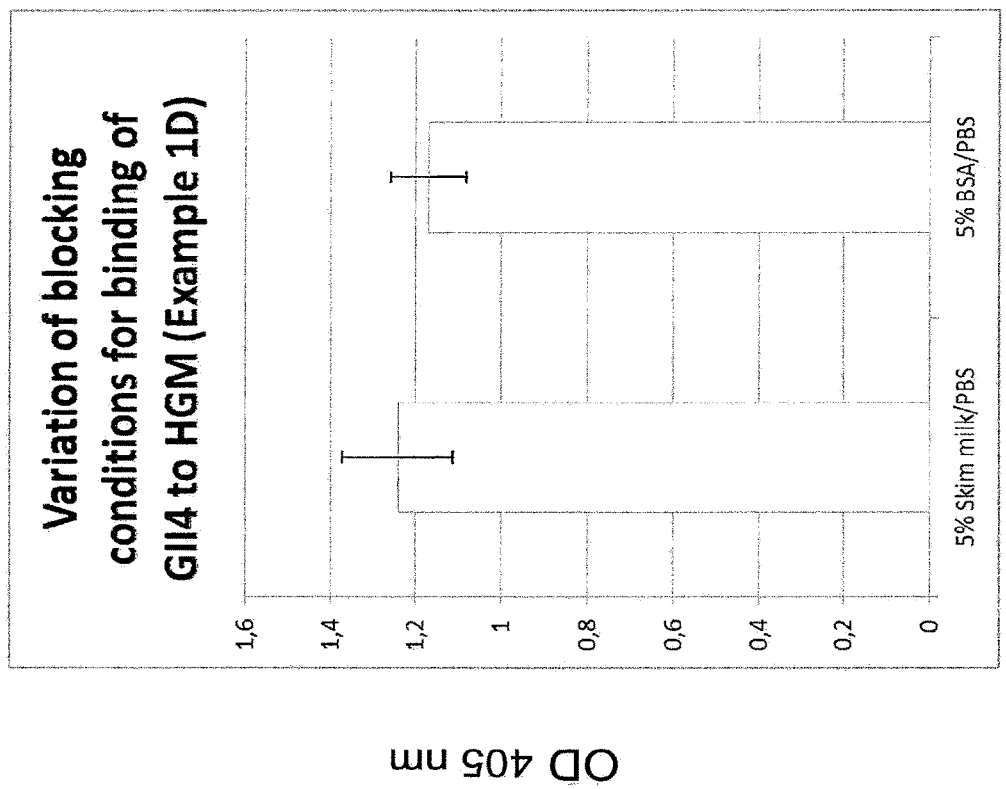

D, Variation of blocking conditions for binding assays of GII.4 to HGM (5% skim milk/PBS vs. 5% BSA/PBS. (FIG. 3.)

Example 2—Inhibition of GII.4 (Sydney, 2012) VLP Binding to HGM (10 µg/Ml) by Native F-Fucoidan, and Desulfated F-Fucoidan from *Fucus Vesiculosus*

Figure 4:
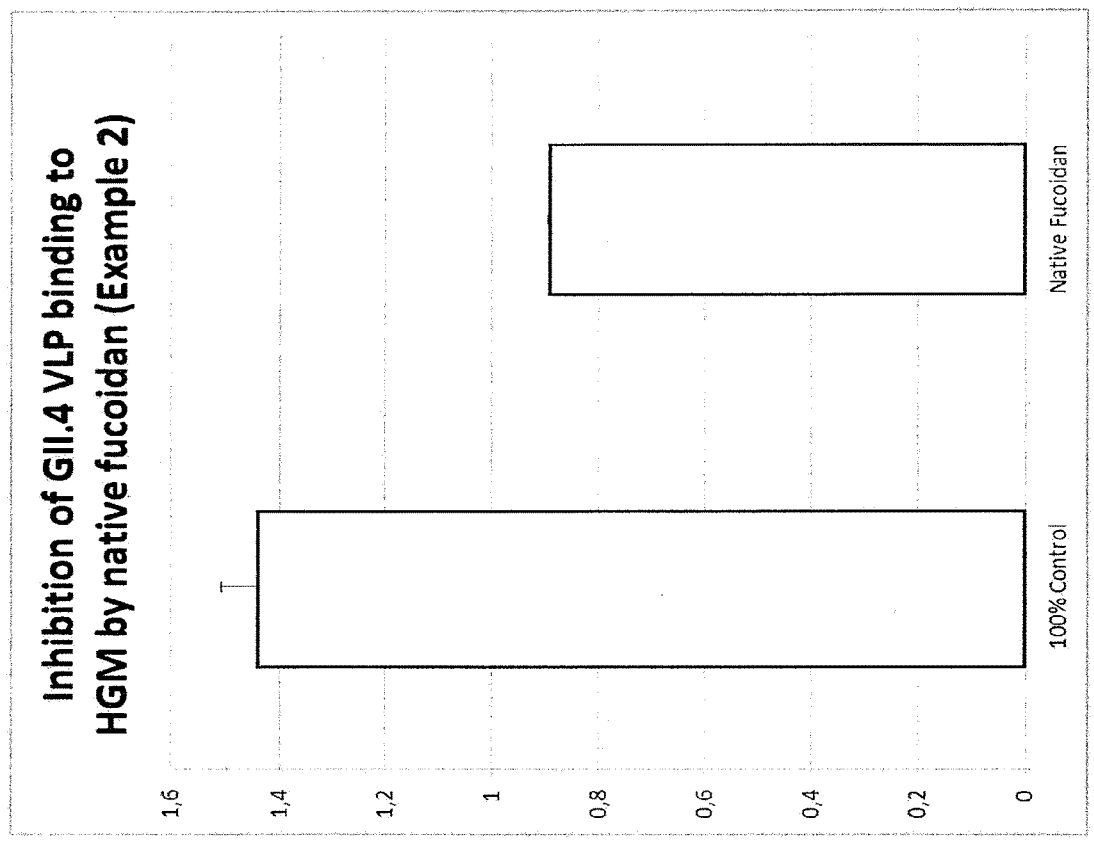

Triplicate assay with fixed inhibitor concentration (10 mg/ml). (FIG. 4.)

Example 3—Inhibition of GII.4 (Sydney, 2012) VLP Binding to HGM (10 µg/Ml) by Processed F-Fucoidan (Processed by Partial Acid Hydrolysis in 0.01 M HCl, 4 h, 60° C., Followed by Neutralization)

Figure 5:
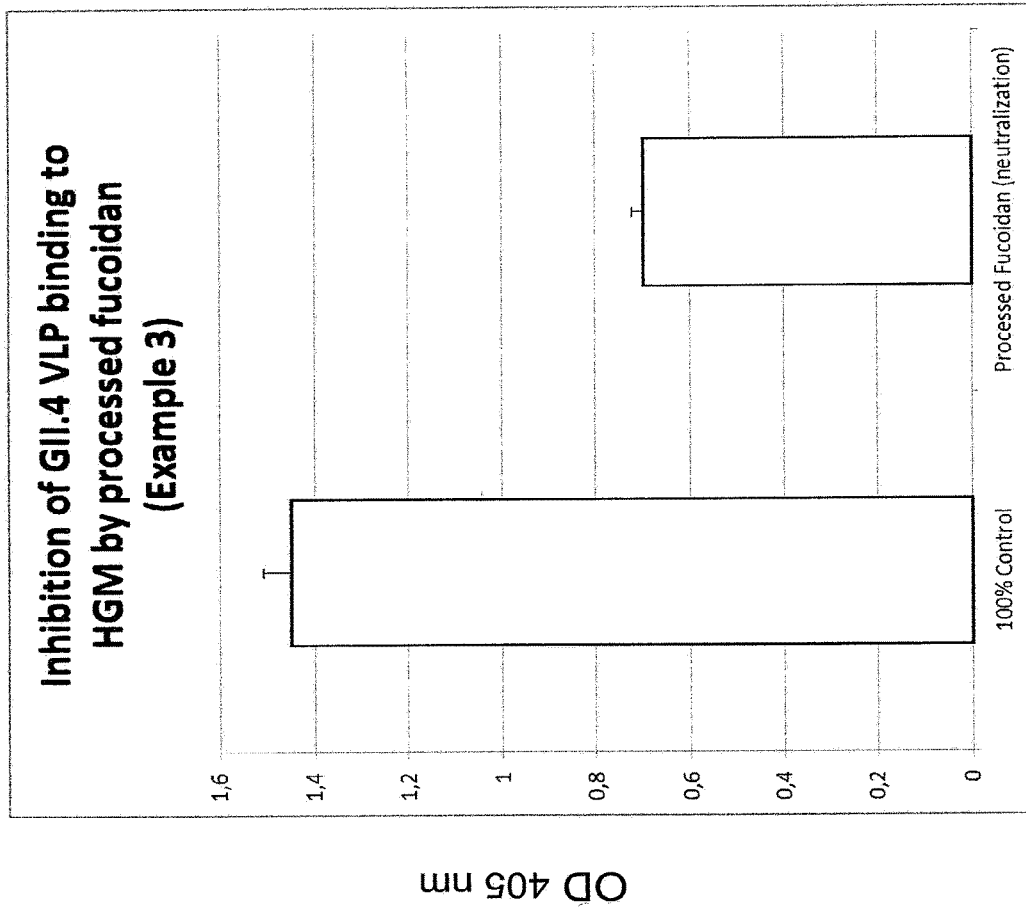

Triplicate assay with fixed inhibitor concentration (5 mg/ml). (FIG. 5.)

Figure 6:
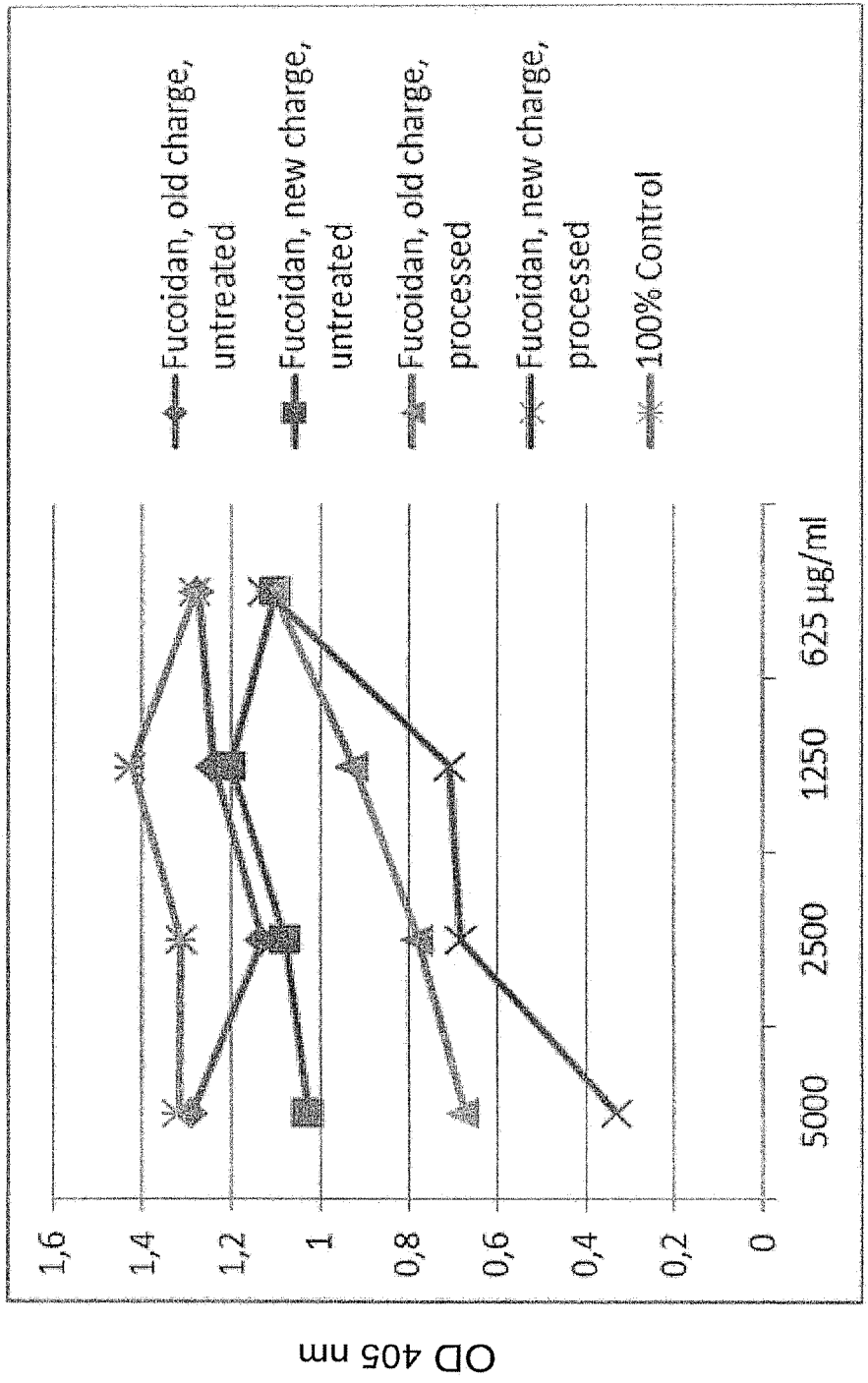

Example 4—Inhibition of GII.4 (Sydney, 2012) VLP Binding to HGM (10 µg/Ml) by Different Charges/Preparations of Native and Processed Fucoidan F-fucoidan stored for over 10 years at 5° C. and a fresh sample (both from Sigma) were tested in duplicate assays (see "old" and "new" charges) after partial acid hydrolysis (0.01 N HCl, 60° C., 4 h), neutralization and solubilization in capsid binding buffer (0.01% Tween-20/PBS) at varying concentrations. (FIG. 6.)

Figure 7:
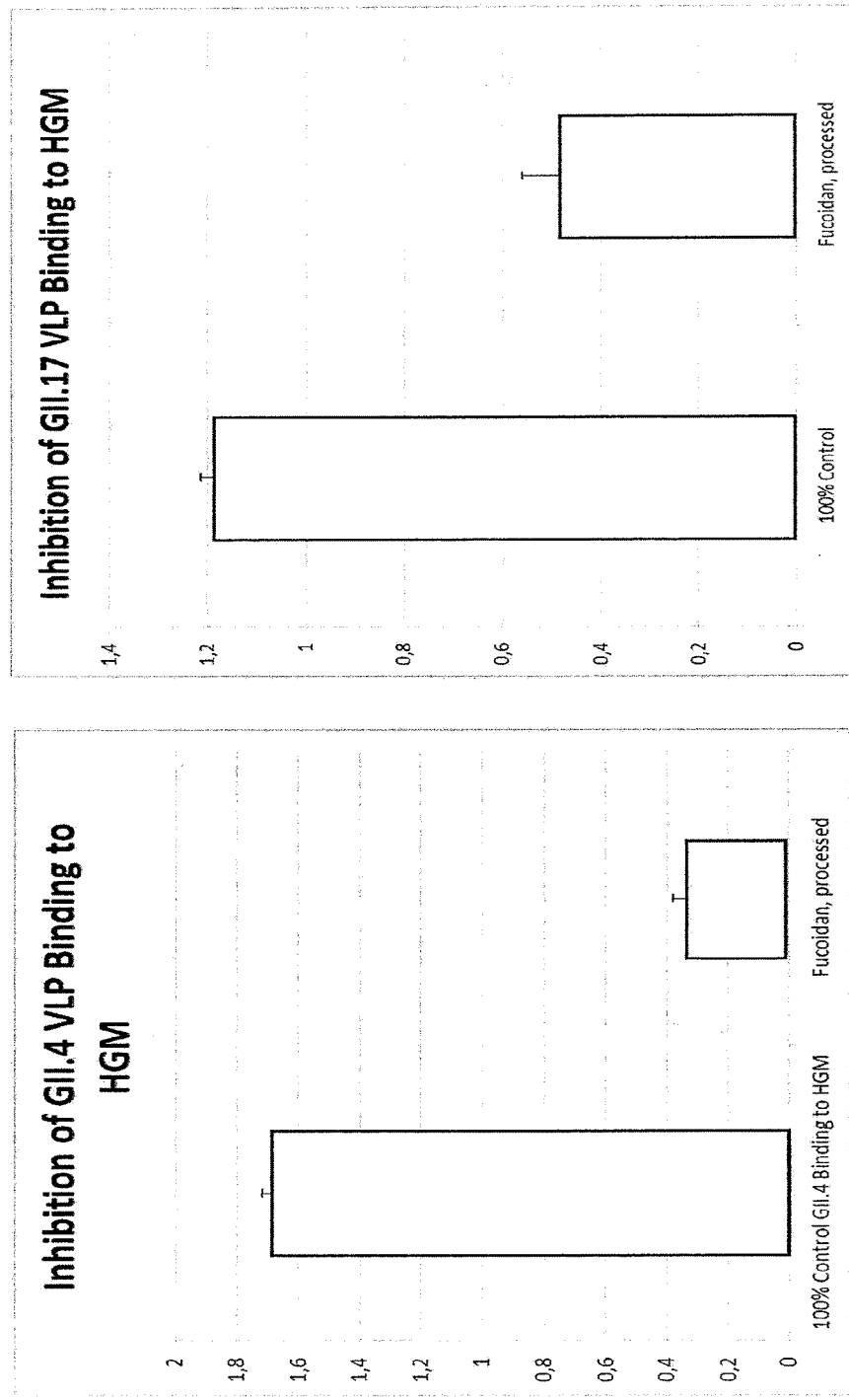
FIG. 7 is bar chart depicting Inhibition of GII.4 (2012) (A), and GII. 17 (2015) (B) VLP binding to HGM by processed fucoidan.

Example 5—Inhibition of GII.4 (2012) (A), and GII.17 (2015) (B) VLP Binding to HGM by Processed Fucoidan Fucoidan from *Fucus vesiculosus* was processed by partial acid hydrolysis with 0.01 N HCl for 4 h at 60° C., neutralized and solubilized after drying in the capsid binding buffer (0.01% Tween-20 in PBS). (FIG. 7.)

Figure 8:
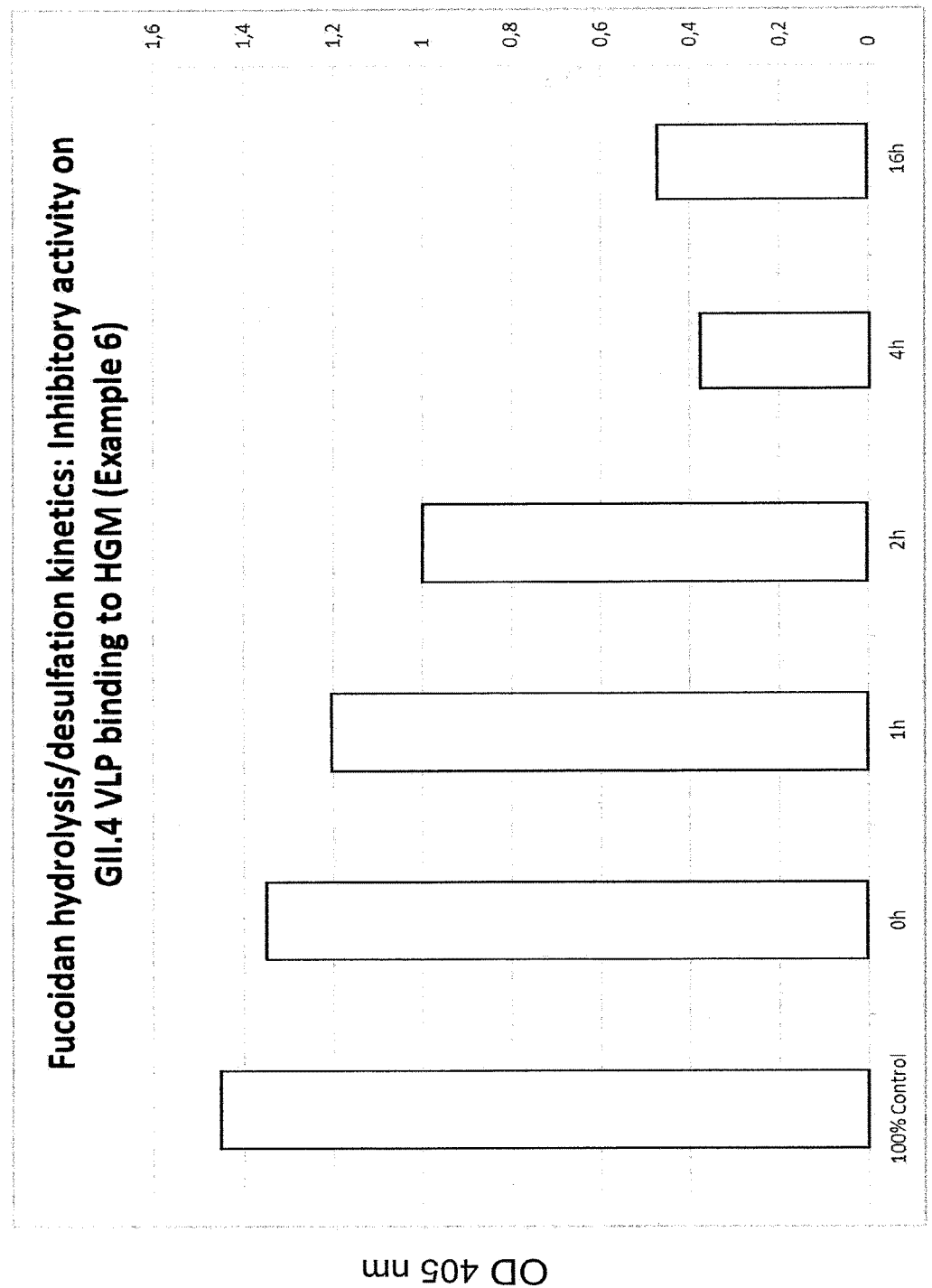
FIG. 8 is a bar chart depicting Time kinetics of fucoidan processing in dilute hydrochloric acid based on binding inhibition assay with GII.4 (Sydney, 2012) VLPs.

Example 6—Time Kinetics of Fucoidan Processing in Dilute Hydrochloric Acid Based on Binding Inhibition Assay with GII.4 (Sydney, 2012) VLPs Fucoidan from *Fucus vesiculosus* was incubated with 0.01 N HCl at 60° C. for increasing reaction times (0-16 h), neutralized with NaOH and tested for inhibitory activity in VLP binding assay with GII.4 capsids as described above. (FIG. 8.)

Example 7—Comparative Evaluation of Different Work-Up Procedures

Figure 9:
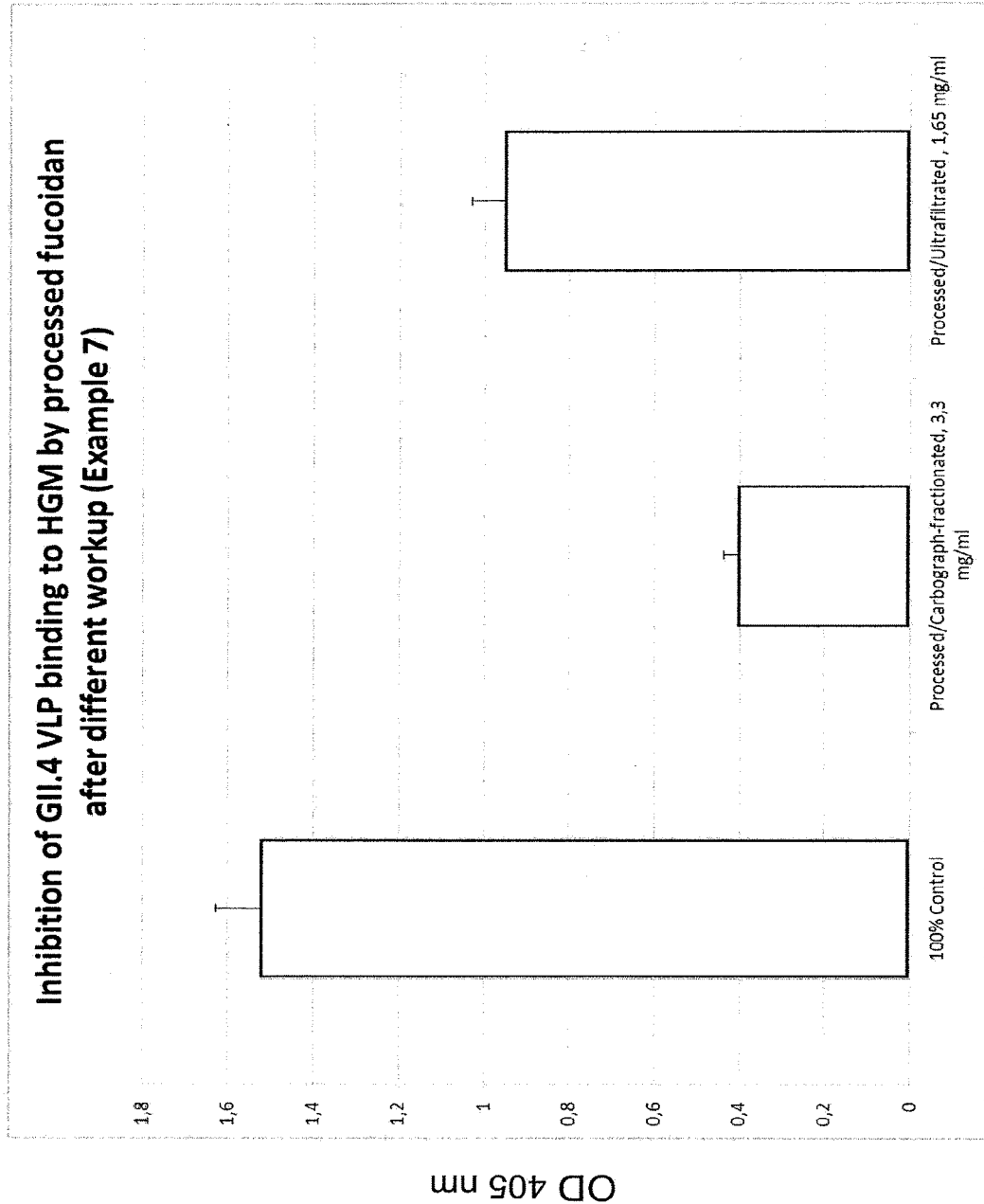
FIG. 9 is a bar chart depicting Comparative evaluation of different work-up procedures including solid-phase extraction on graphitized carbon (150 mg—Carbograph cartridges) and ultrafiltration on cellulose membranes (cutoff 10 kDa)

Workup procedures included solid-phase extraction on graphitized carbon (150 mg-Carbograph cartridges) and ultrafiltration on cellulose membranes (cutoff 10 kDa). Processed fucoidan (concentrations indicated in the graph, FIG. 9.) was tested for inhibitory activity in VLP binding assay with GII.4 capsids as described above.

Example 8—Variation of Acids, their Concentrations and Incubation Times

Figure 10:
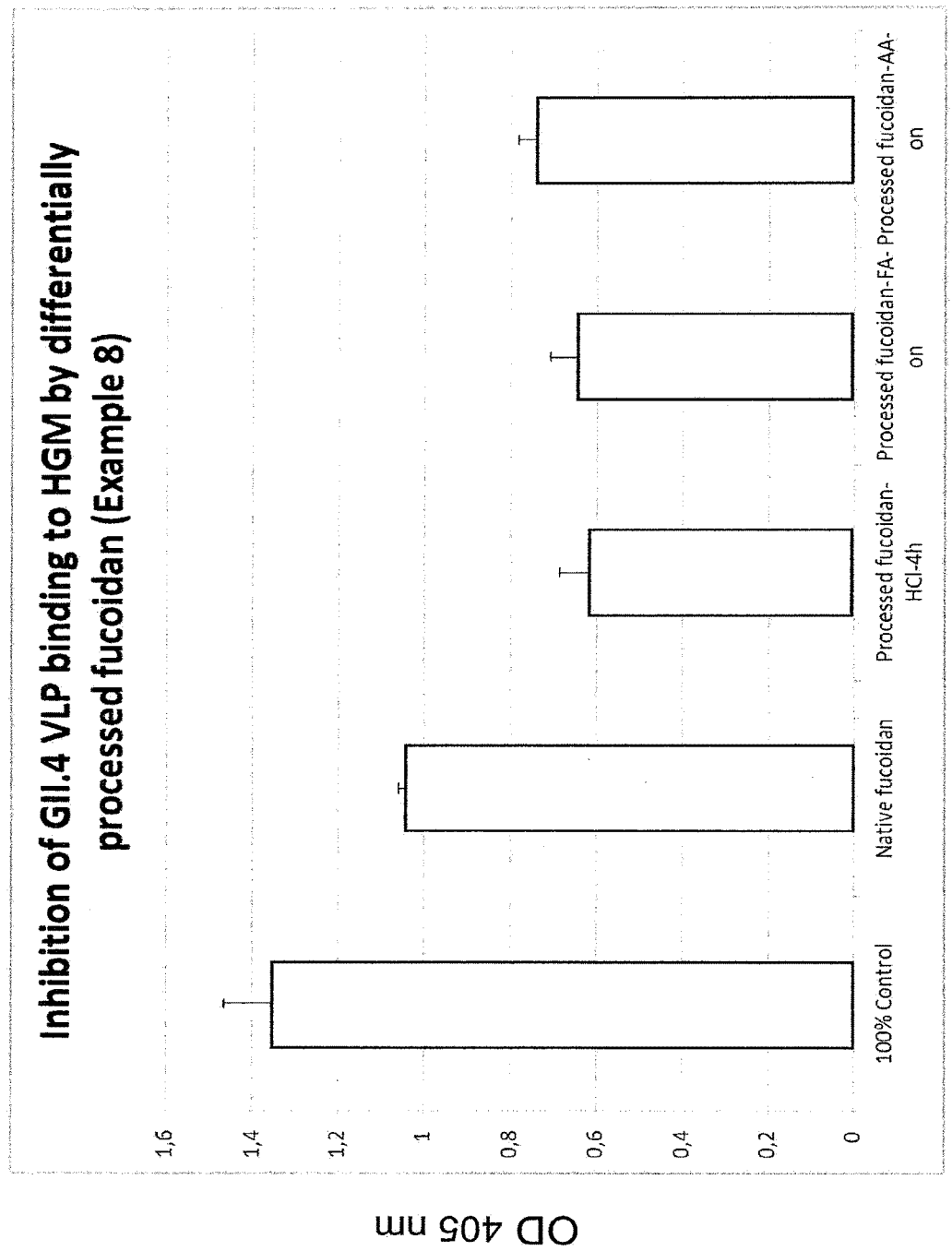
FIG. 10 is bar chart depicting various Fucoidan tested for inhibitory activity in VLP binding assay with GII.4 capsids.

Parameters were 0.01 M HCl (4 h, 60° C.), 0.1 M formic acid (FA) (16 h, 60° C.), 0.1 M acetic acid (AA) (16 h, 60° C.). Processed fucoidan (5 mg/ml) was tested for inhibitory activity in VLP binding assay with GII.4 capsids as described above. (FIG. 10.)

Example 9—Inhibition of GII.4 VLP Binding to HGM by Polystyrenesulfonic Acid Processed Fucoidan (PSSA)

30 mg fucoidan was solubilized in 3 ml water containing 46.7 µl PSSA, filled into a dialysis bag (1 cm diameter, 12 cm length, 6-8 kDa cutoff) and heated to 60° C. over a time period of 18 h. The filtrate was continuously cycled over 580 mg graphitized carbon (flow rate 24 ml/h).

Figure 11:
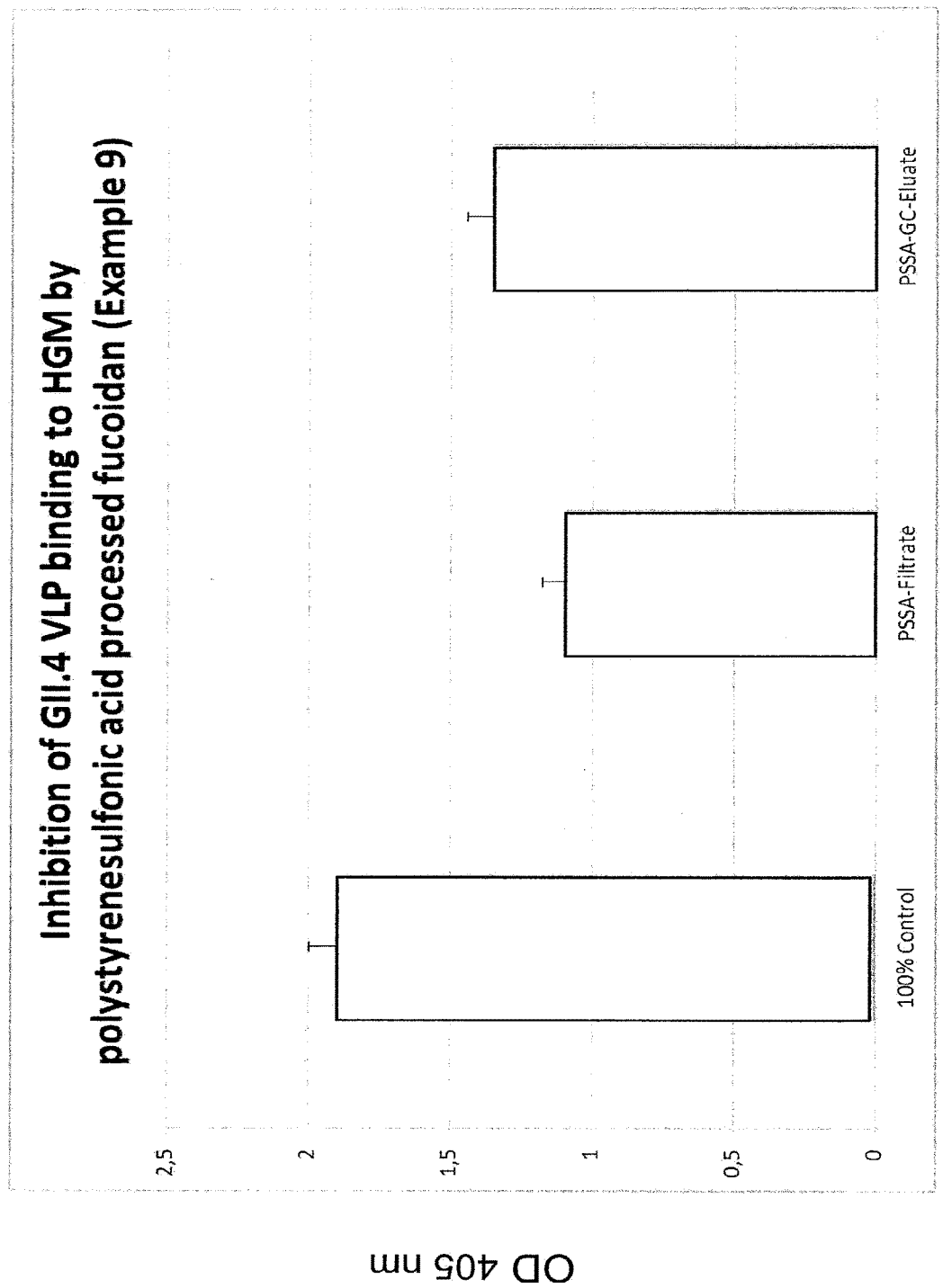
FIG. 11 is bar chart depicting Inhibition of GII.4 VLP binding to HGM by polystyrenesulfonic acidprocessedfucoidan (PSSA)

Elution from graphitized carbon was performed with 80% acetonitrile in water. Most of the filtered oligofucose remained unbound in the dialysis bag (65%), whereas 35% was eluted from the GC column. Each fraction was tested separately (filtrate: 7 mg/ml; GC eluate: 2.9 mg/ml). (FIG. 11.)

Example 10—Fractionation of Fucoidan Processing Products on BioGel-P2

Figure 12:
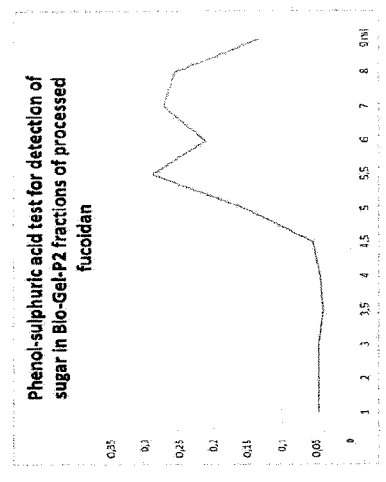
FIG. 12 is a bar chart depicting Fractionation of fucoidan processing products on BioGel-P2.
Figure 12:
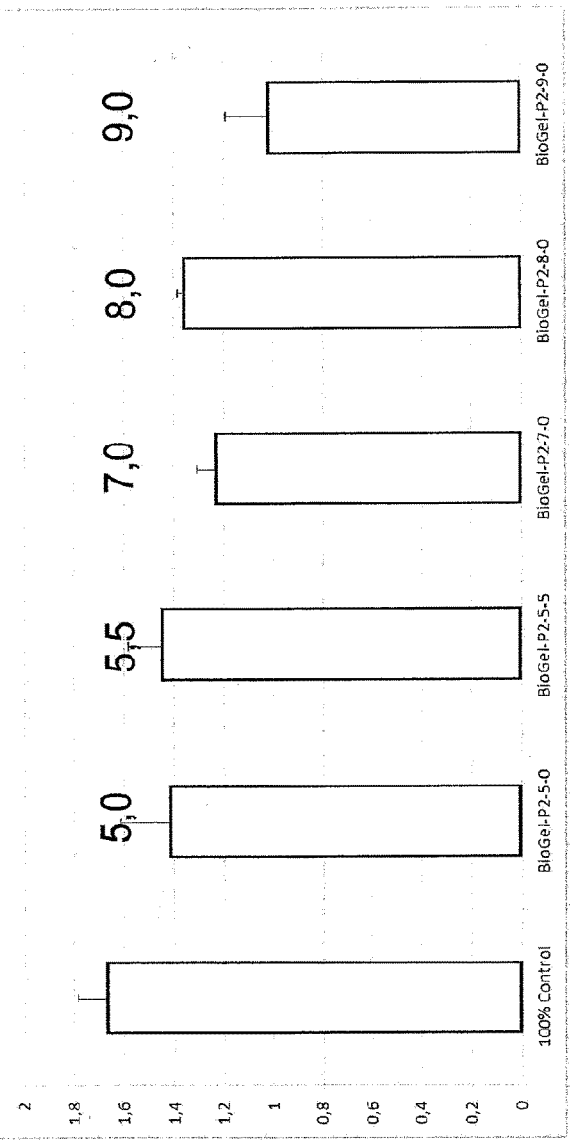

The fractionation on BioGel-P2 column (9.2 ml, 1.4×6 cm) is shown together with results from binding inhibition exerted by glycans in fractions eluted at 5-9 ml in GII.4 VLP binding assay on HGM. The insert (upper panel) shows results from a colorimetric assay of sugars (phenol-sulphuric acid assay). (FIG. 12.)

Example 11—MALDI Mass Spectrometry of Fucoidan Processing Products

Figure 13:
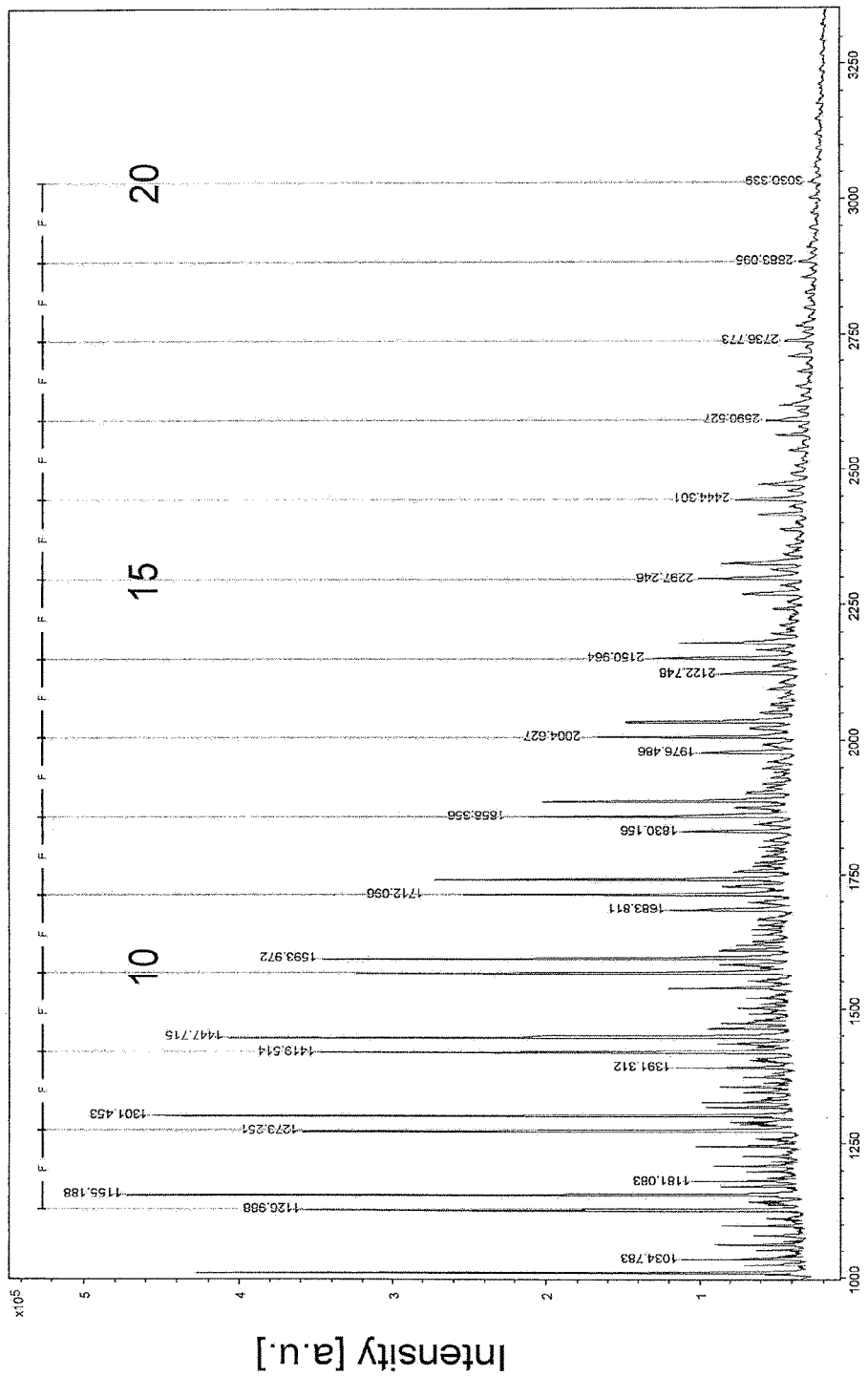
FIG. 13 is a line chart depicting MALDI mass spectrometry of fucoidan processing products.

A, MALDI mass spectrometry on an Ultraflextreme TOF/TOF instrument of permethylated fucoidan processing products after ultrafiltration. Positive ion survey spectrum (MS1). The mass increment of 174 corresponds to a methylated deoxyhexose (indicated by "F"). Oligosaccharides with up to about 20 monosaccharide units were detectable. (FIG. 13.)

Figure 14:
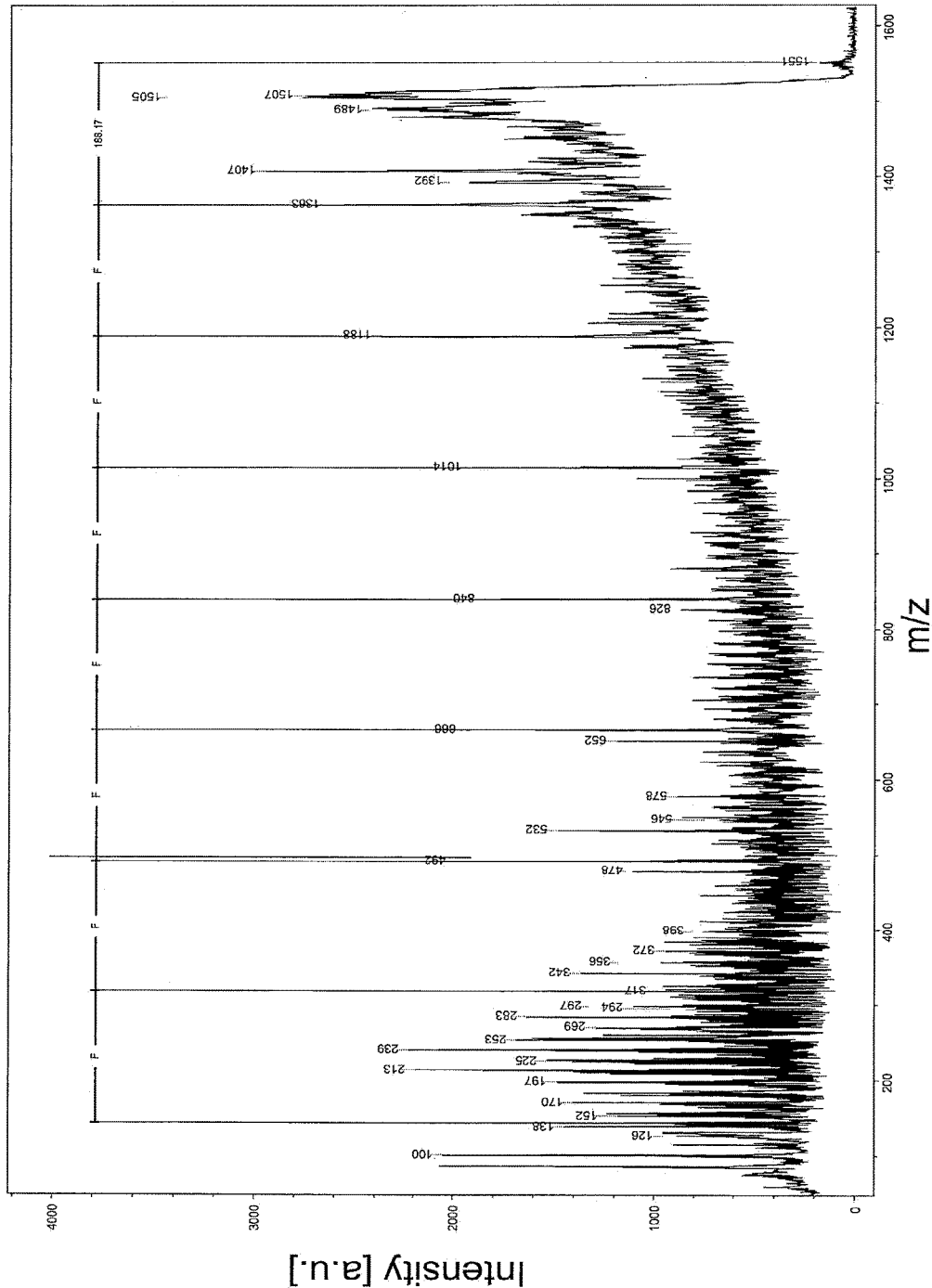
FIG. 14 is a line chart depicting B, MALDI-MS/MS spectrum (Post-Source Decay spectrum in the LIFT modus) of a nonameric oligofucose at m z 1551.

B, MALDI-MS/MS spectrum (Post-Source Decay spectrum in the LIFT modus) of a nonameric oligofucose at m/z 1551. The mass increment of 174 corresponds to a methylated deoxyhexose (indicated by "F"). (FIG. 14.)

Figure 15:
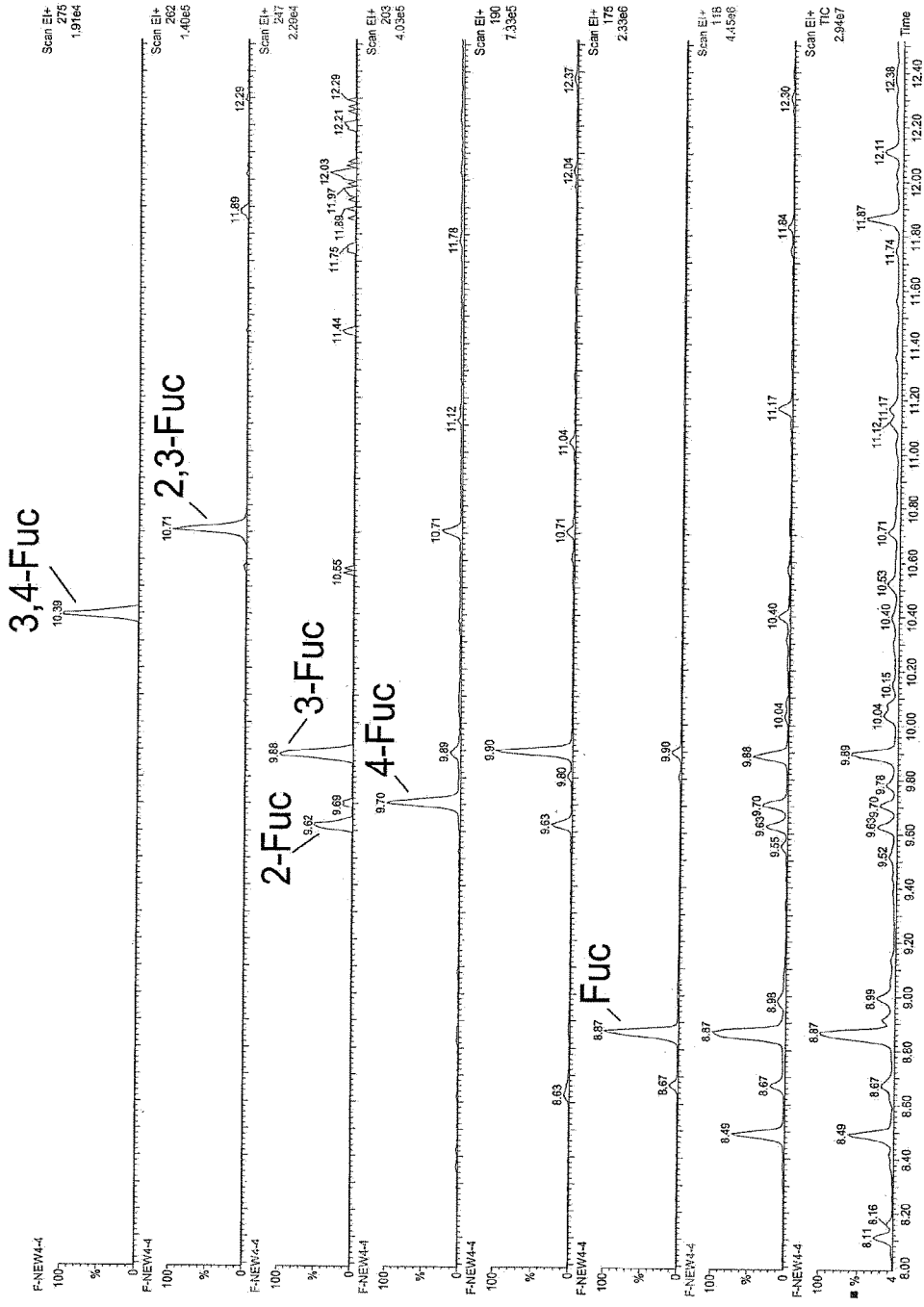
FIG. 15 is a line chart depicting Linkage analysis by GCMS of partially methylated alditol acetates (PMAA) from fucoidan processing products.

Example 12—Linkage Analysis by GCMS of Partially Methylated Alditol Acetates (PMAA) from Fucoidan Processing Products Six different PMAAs were identified in the GC chromatogram (TIC, total ion current) using full-scan spectra and single ion monitoring at m/z 118, 175 (terminal fucose, Fuc), m/z 190 and 247 (2-Fuc, 3-Fuc), m/z 203 (4-Fuc), m/z 262 (2,3-Fuc), and m/z 275 (3,4-Fuc). (FIG. 15.)

The invention claimed is:

1. F-fucoidan comprising desulfated oligosaccharides comprising: terminal fucose alpha-linked by a glycosidic bond as constituents, wherein the oligosaccharides with structural elements Fuc1-2Fuc, Fuc1-3Fuc, Fuc1-4Fuc, Fuc1-2Fuc1-3Fuc, Fuc1-2(Fuc1-4)Fuc, Fuc1-2(Fuc1-3)Fuc, Fuc1-3(Fuc1-2)Fuc and Fuc1-2Fuc1-3Fuc(Fuc1-4)Fuc, and the terminal fucose being exposed at a valency due to branching of oligo- or polysaccharides, wherein the F-fucoidan have anti-viral activity due to competitive inhibitory effect on the norovirus/pathogen binding to blood-group-related glycans on host epithelial mucin, inhibiting pathogen binding to blood-group H related oligosaccharides on epithelia of the gastrointestinal tract, for pathogens causing infections, exhibit competitive activity and accordingly inhibitory effects on binding of enteropathogenic Noroviruses or Rotaviruses, *Salmonella* sp., *Pseudomonas aeruginosa* and *Campylobacter jejuni*, to human H- and Lewis-b blood-group positive epithelial mucins, wherein the desulfation is achieved by inorganic or organic acids, at temperatures and for reaction times that allow effective desulfation and simultaneous fragmentation to the level of oligosaccharides in the size range between 2 and 20 monosaccharide units, or combinations of chemical desulfation/fragmentation with enzymatic treatments with fucoidanases and sulfatases carried out by dialysis from the heated reaction mixture using a soluble, polystyrenesulfonic acid, thereby separating continuously the oligosaccharide products of low masses below a defined membrane cutoff.

2. The F-fucoidan according to claim 1, wherein the F-fucoidan being isolated from *Fucus vesiculosus*, brown algae, seaweed and other marine animals or plants, desulfated and/or processed by partial hydrolysis of the fucoidan polysaccharide that exhibits activity either in native state of sulfation or with a complete or partial loss of sulfate after solvolysis or processing by partial acid hydrolysis.

3. The F-fucoidan according to claim 1, wherein the desulfation is carried out by solvolysis of neutralized, dry F-fucoidan with dimethyl sulfoxide/pyridine, 5:12 (v:v) for 9h at 100° C., followed by dialysis of organic chemicals and drying.

4. The F-fucoidan according to claim 1, wherein F-fucoidan have anti-viral activity due to competitive inhibitory effect on the norovirus/pathogen binding to blood-group-related glycans on host epithelial mucin for the treatment of organisms in industrial farming for the food industry.

5. The F-fucoidan according to claim 1, wherein F-fucoidan is a processed Fucoidan.

* * * * *